(12) United States Patent
Cha et al.

(10) Patent No.: US 9,199,895 B2
(45) Date of Patent: Dec. 1, 2015

(54) METHOD FOR PREPARING 1,3-BUTADIENE AS HIGH YIELD

(75) Inventors: Kyong-Yong Cha, Daejeon (KR);
Dong-Hyun Ko, Daejeon (KR);
Dae-Chul Kim, Daejeon (KR);
Hyun-Seok Nam, Daejeon (KR);
Dae-Heung Choi, Deajeon (KR)

(73) Assignee: LG CHEM, LTD., Seoul (KR)

( * ) Notice: Subject to any disclaimer, the term of this patent is extended or adjusted under 35 U.S.C. 154(b) by 109 days.

(21) Appl. No.: 13/825,439

(22) PCT Filed: Nov. 3, 2011

(86) PCT No.: PCT/KR2011/008338
§ 371 (c)(1),
(2), (4) Date: Jul. 8, 2013

(87) PCT Pub. No.: WO2013/002459
PCT Pub. Date: Jan. 3, 2013

(65) Prior Publication Data
US 2013/0281748 A1    Oct. 24, 2013

(30) Foreign Application Priority Data
Jun. 30, 2011  (KR) .................. 10-2011-0064202

(51) Int. Cl.
*C07C 5/48*  (2006.01)
*C07C 11/167*  (2006.01)
*B01J 8/04*  (2006.01)

(52) U.S. Cl.
CPC ... *C07C 5/48* (2013.01); *B01J 8/04* (2013.01); *B01J 2208/025* (2013.01); *C07C 2523/02* (2013.01); *C07C 2523/04* (2013.01); *C07C 2523/18* (2013.01); *C07C 2523/28* (2013.01); *C07C 2523/31* (2013.01); *C07C 2523/745* (2013.01); *C07C 2523/75* (2013.01); *C07C 2523/887* (2013.01)

(58) Field of Classification Search
USPC ......................................................... 585/302
See application file for complete search history.

(56) References Cited

U.S. PATENT DOCUMENTS

| | | | | |
|---|---|---|---|---|
| 3,764,632 A | * | 10/1973 | Takenaka et al. | 585/622 |
| 4,556,461 A | * | 12/1985 | Ogura et al. | 203/29 |
| 7,417,173 B2 | * | 8/2008 | Crone et al. | 585/325 |
| 2007/0161842 A1 | | 7/2007 | Johann et al. | |
| 2007/0167661 A1 | | 7/2007 | Johann et al. | |
| 2011/0004041 A1 | * | 1/2011 | Chung et al. | 585/628 |

FOREIGN PATENT DOCUMENTS

| | | |
|---|---|---|
| EP | 2256101 A1 | 12/2010 |
| KR | 10-2009-0103424 | 10/2009 |
| KR | 10-2010-0028702 | 3/2010 |
| KR | 10-2010-0042935 | 4/2010 |
| WO | WO 2009119975 A2 * | 10/2009 |

* cited by examiner

*Primary Examiner* — In Suk Bullock
*Assistant Examiner* — Youngsul Jeong
(74) *Attorney, Agent, or Firm* — Dentons US LLP

(57) ABSTRACT

Disclosed is a method for producing 1,3-butadiene through oxidative dehydrogenation of normal-butene using a parallel reactor in which catalysts are charged into fixed bed reactors and are not physically mixed. More specifically, disclosed is a method for efficiently producing 1,3-butadiene through oxidative dehydrogenation of normal-butene using the parallel reactor containing multi-component bismuth molybdate-based catalysts exhibiting different activities to oxidative dehydrogenation for normal-butene isomers (1-butene, trans-2-butene and cis-2-butene), and butene separated from a C4 mixture containing normal-butene and normal-butane, as a reactant.

9 Claims, No Drawings

METHOD FOR PREPARING 1,3-BUTADIENE AS HIGH YIELD

TECHNICAL FIELD

The present invention relates to a method for preparing 1,3-butadiene as a high yield. More specifically, the present invention relates to a method for producing high value 1,3-butadiene using oxidative dehydrogenation of normal-butene by separation applying multi-component bismuth molybdate-based catalysts exhibiting different reaction activities to each of the normal-butene isomers (1-butene, trans-2-butene and cis-2-butene) being able to produce high value 1,3-butadiene into a parallel reactor.

BACKGROUND ART

Methods for producing 1,3-butadiene as many petrochemical product intermediates include naphtha cracking, direct dehydrogenation of normal-butene, and oxidative dehydrogenation of normal-butene. Among such methods, naphtha cracking process entails substantial energy consumption due to a high reaction temperature and requires establishment or expansion of new naphtha crackers to meet an increasing demand for 1,3-butadiene through naphtha cracking. However, this process is not preferred since it is not an exclusive process for production of only 1,3-butadiene, does not optimally match investment and operating for naphtha crackers to production and demand of 1,3-butadiene, and disadvantageously causes production of other feedstock, in addition to 1,3-butadiene.

Accordingly, there is a need for a method for exclusively producing 1,3-butadiene. As an alternative method to naphtha cracking, a method for producing 1,3-butadiene from normal-butene by dehydrogenation has been suggested.

Dehydrogenation of normal-butene includes direct dehydrogenation and oxidative dehydrogenation, which direct dehydrogenation of normal-butene is an endothermic reaction having considerably high reaction heat, is required for high-temperature and low-pressure conditions to produce 1,3-butadiene at a high yield as thermodynamically unfavorable and is not suitable for a commercial process to produce 1,3-butadiene.

On the other hand, oxidative dehydrogenation of the normal-butene is a reaction in which normal-butene reacts with oxygen to produce 1,3-butadiene and water, and is thermodynamically very favorable since stable water is obtained as a kind of products. In addition, oxidative dehydrogenation is exothermic, unlike the direct dehydrogenation of normal-butene, can be obtained in a high-yield 1,3-butadiene at a low reaction temperature, as compared to the direct dehydrogenation and is very suitable for commercialization process as Do not require additional heat supply.

Hence, in spite of the Oxidative dehydrogenation effectively from normal-butene (1-butene, trans-2-butene or cis-2-butene) to 1,3-butadiene alone, it is expected many side reactions such as complete oxidation, since it uses oxygen as a reactant. The reaction mechanism of oxidative dehydrogenation of normal-butene is not yet precisely known, but it is known as C—H bond-cleavage from normal-butene at the same time oxidation-reduction reactions of the catalyst itself and accordingly, catalysts of metal composite oxide type having various oxidation states may be used for the oxidative dehydrogenation.

Accordingly, all the above catalysts are catalysts having a specific crystal structure. Of these, bismuth molybdate-based catalysts and ferrite-based catalysts have been reported to exhibit high activity in oxidative dehydrogenation of normal-butene.

Of these, the bismuth molybdate-based catalysts are pure bismuth molybdate catalyst consisting of solely bismuth and molybdenum oxide and multi-component bismuth molybdate catalyst-added various metals.

It is known that three phases of α-bismuth molybdate ($Bi_2Mo_3O_{12}$), β-bismuth molybdate ($Bi_2Mo_2O_9$) and γ-bismuth molybdate ($Bi_2MoO_6$) of the pure bismuth molybdate catalyst can be used as catalysts. However, 1,3-butadiene manufacturing process by normal-butene oxidative dehydrogenation is unsuitable for commercialization processes due to limit on increase in yield of 1,3-butadiene yield.

Several patents and literatures has ever been reported for multi-component bithmuth molybdate-based catalysts for the oxidative dehydrogenation of normal-butene. Specifically, it is reported to be obtained 1,3-butadiene at a yield of up to 62% by performing oxidative dehydrogenation of a C4 mixture containing normal-butane and normal-butene at 470° C. using complex oxides catalysts consisting of cobalt, iron, bismuth, magnesium, potassium and molybdenum (U.S. Pat. No. 3,998,867), and it is reported to be obtained 1,3-butadiene at a yield of up to 63% by performing oxidative dehydrogenation of 1-butene at 320° C. using complex oxides catalysts consisting of nickel, cobalt, iron, bismuth, phosphorus, potassium and molybdenum (U.S. Pat. No. 3,764,632).

Multi-component bismuth molybdate catalysts stated in the literatures enable production of 1,3-butadiene at a high yield through the oxidative dehydrogenation of 1-butene, but exhibit low activity to 2-butene. On the other hand, ferrite-based catalysts exhibit production of 1,3-butadiene at a high yield through oxidative dehydrogenation of 2-butene, but exhibit low activity to 1-butene.

In order to resolve differences between the reactivity of butene isomers, Korean Patent Publication No. 2009-0103424 suggests bilayer of a multi-component bismuth molybdate catalyst and a ferrite catalyst charged in a reactor, but this method can be affected on yields depending on the composition of the reactants and two kinds of catalysts with different characteristics need to react under the same reaction conditions.

Accordingly, the present inventors were developed catalysts exhibiting different activities depending on isomers using a multi-component bismuth molybdate catalyst and were attempt to maximize the yield of 1,3-butadiene by each charged into the reactor connected in parallel.

DISCLOSURE

Technical Problem

Through extensive research to solve the above mentioned problems, the present inventors was observed that 1,3-butadiene yield can be maximized by suitably using multi-component bismuth molybdate catalysts consisting of only metal components which are highly active to the oxidative dehydrogenation of normal-butene without complex components or undergoing complex processes.

Specifically, the present inventors found that the multi-component bismuth molybdate catalysts exhibited different properties with respect to the oxidative dehydrogenation of normal-butene, such as catalysts consisting of Mo, Bi, Fe, Co and Cs among isomers of normal-butene in the oxidative dehydrogenation of normal-butene exhibited high reactivity to 1-butene, as compared to reactivity to 2-butene and catalysts consisting of Mo, Bi, Fe, Co, Cs and K exhibited higher oxidative dehydrogenation activity to 2-butene.

That is, C4 mixtures used in the present invention contain most normal-butane and normal-butene, and the normal-butene contains three isomers (i.e., 1-butene, trans-2-butene and cis-2-butene) so the present inventors has been completed the present invention by separation applying catalysts having high catalytic reactivity for 1-butene and catalysts having high catalytic reactivity for 2-butene.

It is one object of the present to provide a method for producing 1,3-butadiene with high butene conversion and high 1,3-butadiene selectivity which enables acquisition of 1,3-butadiene at a high yield, at a high butene conversion and high 1,3-butadiene selectivity through the oxidative dehydrogenation of butenes by separation applying two types of catalysts having different response characteristics for normal-butene isomers.

Technical Solution

In accordance with an aspect of the present invention, the above and other objects can be accomplished by the provision of a method for preparing 1,3-butadiene as a high yield comprising the steps of a) charging a first catalyst in a first reactor as a catalyst fixed bed, b) charging a second catalyst into a second reactor connected to the first reactor in parallel as a catalyst fixed bed, simultaneously or sequentially with step (a), c) performing the oxidative dehydrogenation, by passing continuously low-boiling point fraction contained mainly 1-butene obtained a distillation column from a C4 mixture containing normal butene, together with an air and steam through a catalyst layer of the first reactor, while performing the oxidative dehydrogenation, by passing continuously high-boiling point fraction contained mainly 2-butene together with air and steam through a catalyst layer of the second reactor, and d) separating and purifying 1,3-butadiene, the normal-butene and other C4 mixture obtained from the first reactor and the second reactor.

The first catalyst exhibiting good reaction activity for 1-butene is desirable a bismuth molybdate-based catalyst.

More preferably, the first catalyst is prepared by a1) preparing a first solution containing a cesium precursor, a cobalt precursor and an iron precursor, b1) preparing a second solution dissolved a bismuth precursor, c1) preparing a third solution dissolved a molybdenum precursor, d1) adding dropwise the second solution to the first solution, followed by mixing, to prepare a fourth solution, e1) adding dropwise the fourth solution to the third solution to perform co-precipitation solution, f1) stirring the co-precipitation solution for one to two hours and removing moisture to obtain a solid component, and g1) drying the solid component in the range of 150 to 200° C. and thermally treating the solid component in the range of 400 to 600° C. to obtain a catalyst consisting of Mo, Bi, Fe, Co and Cs.

In addition, the second catalyst exhibiting good reaction activity for 2-butene is desirable a potassium bismuth molybdate-based catalyst.

More preferably, the second catalyst is prepared by a2) preparing a first solution containing a potassium precursor, a cesium precursor, a cobalt precursor, an iron precursor and a bismuth precursor, b2) preparing a second solution dissolved a molybdenum precursor, c2) adding dropwise the second solution to the first solution to perform co-precipitation solution, d2) stirring the co-precipitation solution for one to two hours and removing moisture to obtain a solid component, and e2) drying the solid component in the range of 150 to 200° C. and thermally treating the solid component in the range of 400 to 600° C. to obtain a catalyst consisting of Mo, Bi, Fe, Co, Cs and K.

Hereinafter, the present invention will be described in detail.

As described above, the present invention provides a method for obtaining 1,3-butadiene at a high yield through the oxidative dehydrogenation of normal-butene, comprising the steps of separation applying a catalyst exhibiting higher catalytic reactivity for 1-butene than reactivity for 1-butene and a catalyst having high catalytic reactivity for 2-butene, among isomers of normal-butene in parallel reactor, separation supplying butenes exhibiting superior activity per reactors, and performing the oxidative dehydrogenation of normal-butenes to obtain 1,3-butadiene.

The parallel reactor for producing 1,3-butadiene has technical features in consisting of two kinds reactors disposed in parallel so that the catalyst having high catalytic reactivity for 1-butene and the catalyst having high catalytic reactivity for 2-butene can be charged into different reactors, unlike a method using existing single reactor for producing 1,3-butadiene.

Specifically, the term of "C4 mixture" as used herein refers to remaining low-cost C4 Raffinate-3 separated useful compounds from a C4 mixture produced by naphtha cracking, and the C4 raffinate-3 is a C4 mixture consisting of mainly 2-butene (trans-2-butene or cis-2-butene), normal-butane (n-butane) and 1-butene.

The oxidative dehydrogenation of normal-butene are multi-component bismuth molybdate catalysts consisting of five to six kinds of metal components and the multi-component bismuth molybdate catalysts are used a catalyst having good catalytic activity for 1-butene (hereinafter, referred to as a "first catalyst") and a catalyst having good catalytic activity for 2-butene (hereinafter, referred to as a "second catalyst") as described above.

First, the first catalyst is a multi-component bismuth molybdate catalyst consisting of five kinds of metal components including a metal component having a divalent cation, a metal component having a trivalent cation, bismuth and molybdenum as constituent components and depending on the kinds and ratio thereof, the various multi-component bismuth molybdate catalysts may be produced. The metal component having a divalent cation is preferably cesium, cobalt, nickel, manganese and zinc and is used most preferably cesium and cobalt in combination. According to an embodiment of the present invention, multi-component bismuth molybdate catalysts consisting of cobalt, cesium, iron, bismuth and molybdenum exhibit the highest activity to the oxidative dehydrogenation of 1-butene.

In addition, the second catalyst is a multi-component bismuth molybdate catalyst consisting of five kinds of metal components, i.e., a metal component having a monovalent cation, a metal component having a divalent cation, a metal component having a trivalent cation, bismuth and molybdenum as constituent components and depending on the kinds and ratio thereof, the various multi-component bismuth molybdate catalysts may be produced. The metal component having a divalent cation is preferably cesium, cobalt, nickel, manganese and zinc and is used most preferably cesium and cobalt in combination. According to an embodiment of the present invention, multi-component bismuth molybdate catalysts consisting of potassium, cobalt, cesium, iron, bismuth and molybdenum exhibit the highest activity to the oxidative dehydrogenation of 2-butene.

Any metal precursors may be used to produce these first and second catalysts are typically used in the art. The present invention can be used potassium nitrate as the potassium precursor, cesium nitrate as the cesium precursor, cobalt nitrate as the cobalt precursor, iron nitrate as the iron precursor, bismuth nitrate as the bismuth precursor, and ammonium molybdate as the molybdenum precursor, respectively. The precursor ratio is variable, but potassium/cesium/cobalt/iron/bismuth/molybdenum precursor ratio is adjusted to 0-1/0.01-2/1-10/0.5-3/0.5-3/12, preferably 0-0.1/0.01-1/6-9/1-2/1-2/12, in order to maximize 1,3-butadiene yield using the parallel reactor.

The potassium precursor, cesium precursor, cobalt precursor, iron precursor and bismuth precursor are simultaneously dissolved in distilled water, the molybdenum precursor is separately dissolved in distilled water, and then mixed with each other, which depending on the precursor in order to increase the solubility of an acidic solution (for example, a nitric acid) etc. may be added. When the precursors are completely dissolved as solution, the precursor solution containing potassium, cesium, cobalt, iron and bismuth is added to molybdenum contained precursor solution to coprecipitate the metal components therein. The coprecipitated solution is stirred for 0.5 to 24 hours, preferably 2 to 5 hours to realize sufficient coprecipitation.

By removing water from the stirred solution to get a catalyst sample of the solid constituents. The solid catalysts are placed in an electric furnace and thermally treated at a temperature in the range of 300 to 800° C., preferably 400 to 600° C., more preferably 450 to 500° C. to obtain the first catalyst and the second catalyst, respectively.

According to the present invention, each oxidative dehydrogenation reaction for 1-butene and 2-butene proceed the following path such that butenes as reactants are adsorbed on the respective catalysts, oxygen in the catalyst lattice reacts with two hydrogens of the adsorbed butene to produce 1,3-butadiene and water, and molecular oxygens as reactants are filled in an empty oxygen site of the catalyst lattice.

According to an embodiment of the present invention, the first catalyst and the second catalyst exhibit different catalyst activities for 1-butene and 2-butene which are isomers of normal-butene. specifically, the first catalyst exhibits good catalytic reactivity for 1-butene among normal-butene isomers and the second catalyst exhibits good catalytic reactivity for 2-butene.

Thus the present inventors anticipate to maximize the catalytic activity to the oxidative dehydrogenation of normal-butene in the C4 mixture by separation applying two kinds of catalysts having opposite characteristics to normal-butene isomers and could be prepared 1,3-butadiene at a high yield using a parallel reactor to secure advantages of the two catalysts according to embodiments of the present invention.

Then, the present invention provides a method for producing 1,3-butadiene through the oxidative dehydrogenation using a parallel reactor with a multi-component bismuth molybdate-based catalyst and a ferrite-based catalyst with a C4 mixture or C4 raffinate-3 containing a high content of normal butane without additional removal process of normal butane and separation processes of normal-butene, as a source of normal-butene.

In the experiments of the present invention, the first catalyst and the second catalyst are charged for each of two kinds of shell and tube reactors connected in parallel for catalyst reaction, the reactors are installed inside an electric furnace, a reaction temperature maintains constant, and amounts of catalysts are set_ based on the normal-butene, to satisfy a gas hourly space velocity (GHSV) in the range of 50 to 5000 h$^{-1}$, preferably 100 to 1000 h$^{-1}$, more preferably 150 to 500 h$^{-1}$.

At this time, a weight ratio of 1-butene to 2-butene of a 1-butene-containing low-boiling point fraction, and a weight ratio of 1-butene to 2-butene of a 2-butene-containing high-boiling point fraction supplied in the each reactor are preferably in the range of 10:0 to 8:2 and in the range of 0:10 to 1:9, respectively, and are more preferably, in the range of 9.9:0.1 to 8.5:1.5 and in the range of 0.05:9.95 to 0.75 to 9.25, respectively, considering a final total yield.

Reactants into the reactor connected in parallel use separated 1-butene or 2-butene, oxygen, nitrogen and steam, and a ratio of the charged butene, oxygen, nitrogen and steam is set to in the range of 1:0.5~2:1~50:1~50, preferably 1:0.5~1:10~30:10~30.

The amounts of butene and the other reactant air used herein are precisely controlled using a mass flow controller, and liquid water is supplied to each reactor using a syringe pump, vaporized to steam injection. Liquid water injected parts maintains a temperature in the range of 150 to 300° C., preferably 180 to 250° C., the water supplied by the syringe pump immediately vaporized into steam and the other reactants (C4 mixture and air) where liquid water is completely mixed is passed through the catalyst layers.

When the first catalyst and the second catalyst are separately applied using the parallel reactor according to the present invention, 1,3-butadiene can be obtained at a high yield at a high butene conversion and high 1,3-butadiene selectivity through the oxidative dehydrogenation of butene.

Advantageous Effects

The present invention appears the first catalysts exhibit good catalytic reactivity for 1-butene, among isomers of normal-butene, as compared to reactivity for 2-butene, and, unlike the first catalysts, the second catalysts exhibit good oxidative dehydrogenation activity for 2-butene, as compared to reactivity for 1-butene, and thus provides a method for preparing 1,3-butadiene as a high yield, at a higher butene conversion and at higher selectivity through the oxidative dehydrogenation of normal-butene at the same time by separation applying a first catalyst exhibiting good catalytic reactivity for 1-butene and a second catalyst exhibiting good catalytic reactivity for 2-butene. It has the advantage that it can be applied directly in the commercialization process.

Unlike existing 1,3-butadiene production process using naphtha cracking, the catalyst process according to the present invention is a process for producing 1,3-butadiene alone through the oxidative dehydrogenation of normal-butene, thus is able to cope with the advantage of being able to produce optimized according to market demand. In addition, the method has many advanates in terms of utilization of ole, that is in terms of energy by direct production of 1,3-butadiene, which is highly useful in the petrochemical industry, from a C4 mixture or C4 raffinate-3 worth less in the petrochemical industry, thus achieve high utilization of the low price of C4 oil components.

BEST MODE

Hereafter, through the embodiment of the present invention to be described in more detail one, are not intended to limit the scope of the present invention.

PREPARATION EXAMPLE 1

First Catalyst Preparation-1

Cesium nitrate (CsNO$_3$) was used as a cesium precursor, cobalt nitrate hexahydrate (Co(NO$_3$)$_2$.6H$_2$O) was used as a cobalt precursor, iron nitrate nonahydrate (Fe(NO$_3$)$_3$.9H$_2$O) was used as an iron precursor, bismuth nitrate pentahydrate (Bi(NO$_3$)$_2$.5H$_2$O) was used as a bismuth precursor, and ammonium molybdate tetrahydrate ((NH$_4$)6Mo$_7$O$_{24}$.4H$_2$O) was used as a molybdenum precursor. Other metal precursors were well dissolved in distilled water, but bismuth nitrate pentahydrate was well dissolved in a strong acidic solution. Accordingly, bismuth nitrate pentahydrate was apart dissolved by the addition of nitric acidic solution in distilled water.

To produce a first catalyst, a molar ratio of molybdenum:bismuth:iron:cobalt:cesium was set at 12:1:2:7:0.6.

18.0 g of cesium nitrate hydrate (CsNO$_3$) as the cesium precursor, 320.8 g of cobalt nitrate hexahydrate (Co(NO$_3$)$_2$.6H$_2$O) and 125.9 g of iron nitrate nonahydrate (Fe(NO$_3$)$_3$.9H$_2$O) were dissolved in 250 mL of distilled water, followed by stirring. Separately, 75.6 g of bismuth nitrate pentahydrate (Bi(NO$_3$)$_2$.5H$_2$O) was added to a solution of 22.7 g of nitric acid in 75 mL of distilled water, followed by dissolving with stirring. After confirming that the bismuth has completely dissolved, the bismuth solution was added to a solution containing cesium precursor, cobalt precursor and iron precursor, to prepared an acidic solution containing cesium precursor, cobalt precursor, iron precursor and bismuth precursor dissolved therein.

In addition, 326.9 g of ammonium molybdate tetrahydrate ((NH$_4$)$_6$Mo$_7$O$_{24}$.4H$_2$O) was apart dissolved in 1,300 mL of distilled water, followed by stirring, to separately produce a molybdate solution. The acidic solution containing dissolved nickel precursor, iron precursor and bismuth precursor was dropwise added to the molybdate solution.

The resulting mixed solution was stirred at room temperature for one hour using a magnetic stirrer and the precipitated solution was dried at 120° C. for 24 hours to obtain a solid sample. The solid sample was crushed, mixed with water and extruded into a cylindrical shape of a diameter 6 mm and a length 6 mm, and the produced extrusion material was thermally treated while maintaining a temperature of 450° C. in an electric furnace to produce a first catalyst having a composition of Mo$_{12}$Bi$_1$Fe$_2$Co$_7$Cs$_{0.6}$O$_x$.

This catalyst is referred to as "BDP-125" herein.

The catalyst was X-ray diffraction analysis, and inductively coupled plasma atomic emission spectrometry (ICP-AES), and as a result, the catalyst was successful manufacturing. The first catalyst was found to be a mixed phase of β-CoMoO$_4$, Fe$_2$(MoO$_4$)$_3$, α-Bi$_2$Mo$_3$O$_{12}$, and γ-Bi$_2$MoO$_6$ through X-ray diffraction analysis, and was confirmed that desired amounts of metal precursors were exactly co-precipitated within the range of analytical error through ICP-AES analysis.

PREPARATION EXAMPLE 2

Second Catalyst Preparation-1

Potassium nitrate (KNO$_3$) was used as a potassium precursor, cesium nitrate (CsNO$_3$) was used as a cesium precursor, cobalt nitrate hexahydrate (Co(NO$_3$)$_2$.6H$_2$O) was used as a cobalt precursor, iron nitrate nonahydrate (Fe (NO$_3$)$_3$.9H$_2$O) was used as an iron precursor, bismuth nitrate pentahydrate (Bi(NO$_3$)$_2$.5H$_2$O) was used as a bismuth precursor, and ammonium molybdate tetrahydrate ((NH$_4$) 6Mo$_7$O$_{24}$.4H$_2$O) was used as a molybdenum precursor. water, but bismuth nitrate pentahydrate was well dissolved in a strong acidic solution. Accordingly, bismuth nitrate pentahydrate was apart dissolved by the addition of nitric acidic solution in distilled water.

To produce a second catalyst, a molar ratio of molybdenum:bismuth:iron:cobalt:cesium:potassium was set to 12:1:1:7:0.15:0.06.

105.9 g of bismuth nitrate pentahydrate (Bi(NO$_3$)$_2$.5H$_2$O) was added to a solution of 33.0 g of nitric acid in 28 mL of distilled water, followed by dissolving with stirring. After confirming that the bismuth has completely dissolved, a solution containing 6.4 g of cesium nitrate hydrate (CsNO$_3$) as the cesium precursor, 1.3 g of potassium nitrate (KNO$_3$) as the potassium precursor, 449.3 g of cobalt nitrate hexahydrate (Co(NO$_3$)$_2$.6H$_2$O) and 88.2 g of iron nitrate nonahydrate (Fe(NO$_3$)$_3$.9H$_2$O) was prepared.

In addition, 462.5 g of ammonium molybdate tetrahydrate ((NH$_4$)$_6$Mo$_7$O$_{24}$.4H$_2$O) was apart dissolved in 1,150 mL of distilled water, followed by stirring, to separately prepare a molybdate solution. The acidic solution containing dissolved nickel precursor, iron precursor and bismuth precursor was dropwise added to the molybdate solution.

The resulting mixed solution was stirred at room temperature for one hour using a magnetic stirrer and the precipitated solution was dried at 120° C. for 24 hours to obtain a solid sample. The solid sample was crushed, mixed with water and extruded into a cylindrical shape of a diameter 6 mm and a length 6 mm. The produced extrusion material was thermally treated while maintaining a temperature of 450° C. in an electric furnace to produce a first catalyst having a formula of Mo$_{12}$Bi$_1$Fe$_1$Co$_7$Cs$_{0.15}$K$_{0.06}$O$_x$.

This catalyst is referred to as "BDP-142" herein.

The catalyst was X-ray diffraction analysis, and inductively coupled plasma atomic emission spectrometry (ICP-AES), and as a result, the catalyst was successful manufacturing. The second catalyst was found to be a mixed phase of β-CoMoO$_4$, Fe$_2$(MoO$_4$)$_3$, α-Bi$_2$Mo$_3$O$_{12}$, and γ-Bi$_2$MoO$_6$ through X-ray diffraction analysis, and was confirmed that desired amounts of metal precursors were exactly co-precipitated within the range of analytical error through ICP-AES analysis.

PREPARATION EXAMPLE 3

Second Catalyst Preparation-2

Potassium nitrate (KNO$_3$) was used as a potassium precursor, cesium nitrate (CsNO$_3$) was used as a cesium precursor, cobalt nitrate hexahydrate (Co(NO$_3$)$_2$.6H$_2$O) was used as a cobalt precursor, iron nitrate nonahydrate (Fe (NO$_3$)$_3$. 9H$_2$O) was used as an iron precursor, bismuth nitrate pentahydrate (Bi(NO$_3$)$_2$.5H$_2$O) was used as a bismuth precursor, and ammonium molybdate tetrahydrate ((NH$_4$)$_6$Mo$_7$O$_{24}$.4H$_2$O) was used as a molybdenum precursor.

To produce a second catalyst, a molar ratio of molybdenum:bismuth:iron:cobalt:cesium:potassium was set at 12:1:1:7:0.07:0.06.

105.9 g of bismuth nitrate pentahydrate (Bi(NO$_3$)$_2$.5H$_2$O) was added to acid in 28 mL of distilled water added 33.0 g of nitric acid, followed by dissolving with stirring. After confirming that the bismuth has completely dissolved, a solution containing 3.0 g of cesium nitrate hydrate (CsNO$_3$) as the cesium precursor, 1.3 g of potassium nitrate (KNO$_3$) as the potassium precursor, 449.3 g of cobalt nitrate hexahydrate (Co(NO$_3$)$_2$.6H$_2$O) and 88.2 g of iron nitrate nonahydrate (Fe(NO$_3$)$_3$.9H$_2$O) was prepared.

In addition, 462.5 g of ammonium molybdate tetrahydrate ((NH$_4$)$_6$Mo$_7$O$_{24}$.4H$_2$O) was apart dissolved in 1,150 mL of distilled water, followed by stirring, to separately prepare a molybdate solution. The acidic solution containing dissolved nickel precursor, iron precursor and bismuth precursor was dropwise added to the molybdate solution.

The resulting mixed solution was stirred at room temperature for one hour using a magnetic stirrer and the precipitated solution was dried at 120° C. for 24 hours to obtain a solid sample. The solid sample was crushed, mixed with water and extruded into a cylindrical shape of a diameter 6 mm and a length 6 mm. The produced extrusion material was thermally treated while maintaining a temperature of 450° C. in an electric furnace to produce a second catalyst having a formula of $Mo_{12}Bi_1Fe_1Co_7Cs_{0.07}K_{0.06}O_x$.

The catalyst was referred to as "BDP-143".

The catalyst was X-ray diffraction analysis, and inductively coupled plasma atomic emission spectrometry (ICP-AES), and as a result, the catalyst was successful manufacturing. The second catalyst was found to be a mixed phase of $\beta$-$CoMoO_4$, $Fe_2(MoO_4)_3$, $\alpha$-$Bi_2Mo_3O_{12}$, and $\gamma$-$Bi_2MoO_6$ through X-ray diffraction analysis, and was confirmed that desired amounts of metal precursors were exactly co-precipitated within the range of analytical error through ICP-AES analysis.

PREPARATION EXAMPLE 4

Second Catalyst Preparation-3

Potassium nitrate ($KNO_3$) was used as a potassium precursor, cesium nitrate ($CsNO_3$) was used as a cesium precursor, cobalt nitrate hexahydrate ($Co(NO_3)_2.6H_2O$) was used as a cobalt precursor, iron nitrate nonahydrate (Fe $(NO_3)_3.9H_2O$) was used as an iron precursor, bismuth nitrate pentahydrate ($Bi(NO_3)_2.5H_2O$) was used as a bismuth precursor, and ammonium molybdate tetrahydrate (($NH_4)_6Mo_7O_{24}.4H_2O$) was used as a molybdenum precursor.

In order to produce a second catalyst, a molar ratio of molybdenum:bismuth:iron:cobalt:cesium:potassium was set at 12:1:1:7:0.03:0.06.

105.9 g of bismuth nitrate pentahydrate ($Bi(NO_3)_2.5H_2O$) was added to 28 mL of distilled water added 33.0 g of a nitric acid, followed by dissolving with stirring. After confirming that the bismuth has completely dissolved, a solution containing 1.3 g of cesium nitrate hydrate ($CsNO_3$) as the cesium precursor, 1.3 g of potassium nitrate ($KNO_3$) as the potassium precursor, 449.3 g of cobalt nitrate hexahydrate ($Co(NO_3)_2.6H_2O$) and 88.2 g of iron nitrate nonahydrate (Fe $(NO_3)_3.9H_2O$) was prepared.

In addition, 462.5 g of ammonium molybdate tetrahydrate (($NH_4)_6Mo_7O_{24}.4H_2O$) was apart dissolved in 1,150 mL of distilled water, followed by stirring, to separately prepare a molybdate solution. The acidic solution containing dissolved nickel precursor, iron precursor and bismuth precursor was dropwise added to the molybdate solution.

The resulting mixed solution was stirred at room temperature for one hour using a magnetic stirrer and the precipitated solution was dried at 120° C. for 24 hours to obtain a solid sample. The solid sample was crushed, mixed with water and extruded into a cylindrical shape of a diameter 6 mm and a length 6 mm. The produced extrusion material was thermally treated while maintaining a temperature of 450° C. in an electric furnace to produce a second catalyst having a formula of $Mo_{12}Bi_1Fe_1Co_7Cs_{0.03}K_{0.06}O_x$.

The catalyst was referred to as "BDP-146".

The catalyst was X-ray diffraction analysis, and inductively coupled plasma atomic emission spectrometry (ICP-AES), and as a result, the catalyst was successful manufacturing. The second catalyst was found to be a mixed phase of $\beta$-$CoMoO_4$, $Fe_2(MoO_4)_3$, $\alpha$-$Bi_2Mo_3O_{12}$, and $\gamma$-$Bi_2MoO_6$ through X-ray diffraction analysis, and was confirmed that desired amounts of metal precursors were exactly co-precipitated within the range of analytical error through ICP-AES analysis.

EXAMPLE 1

Two kinds of shell and tube reactors of first reactor and second reactor were connected in parallel, and the first reactor filled with BDP 125 catalyst produced in Preparation Example 1 was charged into a first reactor and the second reactor charged with BDP 142 catalyst produced in Preparation Example 2.

For sake of comparison, the contents of charged catalysts were controlled such that a volume ratio of respective catalysts with respect to a volume of the catalyst used for a single layer reaction was 1:2 ratio to match the total amount of the volume of a single layer of catalytic reaction and a total volume of catalysts used in the parallel reaction (Total 200 ml, 66.7 ml for the first reactor, and 133.3 ml for the second reactor).

Then, a C4 mixture containing 1-butene, trans-2-butene and cis-2-butene at a ratio of 1:1:1 as normal butene isomers was passed through a two-stage distillation tower having a column plate number of 200 and a 1-butene-containing low-boiling point fraction and a 2-butene-containing high-boiling point fraction were supplied together with air and steam to the first reactor and the second reactor, respectively. A ratio of oxygen to normal-butene was 0.75, a ratio of steam to normal-butene was 15, and a ratio of nitrogen to normal-butene was 15.

A content of 2-butene present in the 1-butene-containing low-boiling point fraction was lower than 1% and a content of 1-butene present in the high-boiling point fraction was 0.5% or less.

The type of reactants supplied into the each reactor, reaction temperature and normal-butene conversion, 1,3-butadiene selectivity and 1,3-butadiene yield were calculated and the results are set forth in the following Table 1.

EXAMPLE 2

The same process as in Example 1 was performed, except that a content of 2-butene present in the 1-butene-containing low-boiling point fraction was 10% or less, and a content of 1-butene present in the high-boiling point fraction was 5% or less.

EXAMPLE 3

The same process as in Example 1 was performed, except that a content of 2-butene present in the 1-butene-containing low-boiling point fraction was lower than 15%, and a content of 1-butene present in the high-boiling point fraction was 7.5% or less.

EXAMPLE 4

The same process as in Example 1 was performed, except that a BDP 143 catalyst was charged into the second reactor.

EXAMPLE 5

The same process as in Example 1 was performed, except that the BDP 146 catalyst was charged into the second reactor.

COMPARATIVE EXAMPLE 1

The same process as in Example 1 was performed, except that the first reactor, into which the BDP 125 catalyst was charged as the first catalyst, was exclusively used, and the C4 mixture containing normal-butene was directly injected into the first reactor, without a separation process using a distillation tower.

COMPARATIVE EXAMPLE 2

The same process as in Example 1 was performed, except that the second reactor, into which the BDP 142 catalyst was charged as the second catalyst, was exclusively used, and the C4 mixture containing normal-butene was directly injected into the second reactor, without a separation process using a distillation tower.

COMPARATIVE EXAMPLE 3

The same process as in Example 1 was performed, except that the second reactor, into which the BDP 143 catalyst was charged as the second catalyst, was exclusively used, and the C4 mixture containing normal-butene was directly injected into the second reactor, without a separation process using a distillation tower.

COMPARATIVE EXAMPLE 4

The same process as in Example 1 was performed, except that the second reactor, into which the BDP 146 catalyst was charged as the second catalyst, was exclusively used, and the C4 mixture containing normal-butene was directly injected into the second reactor, without a separation process using a distillation tower.

Conversion, selectivity and yield shown in the following table 1 were calculated in accordance with the following Equations 1, 2 and 3.

$$\text{Conversion (\%)} = \frac{\text{Number of moles of reacted normal-butene}}{\text{Number of moles of supplied normal-butene}} \times 100 \quad \text{Equation 1}$$

$$\text{Selectivity (\%)} = \frac{\text{Number of moles of produced 1.3-butadiene}}{\text{Number of moles of reacted normal-butene}} \times 100 \quad \text{Equation 2}$$

$$\text{Yield (\%)} = \frac{\text{Number of moles of produced 1.3-butadiene}}{\text{Number of moles of supplied normal-butene}} \times 100 \quad \text{Equation 3}$$

TABLE 1

| Items | Reactor | Catalyst | Major reactant (isomer, weight ratio) | Reaction temperature (° C.) | Conversion ratio | Selectivity | Yield |
|---|---|---|---|---|---|---|---|
| Ex. 1 | First reactor | BDP-125 | 1-butene (1%)* | 320 | 99.6 | 94.2 | 93.8 |
| | Second reactor | BDP-142 | 2-butene (0.5%)** | 340 | 85.0 | 91.2 | 77.5 |
| | | | Total | | 89.9 | 92.2 | 82.9 |
| Ex. 2 | First reactor | BDP-125 | 1-butene (10%) | 320 | 91.1 | 94.4 | 85.9 |
| | Second reactor | BDP-142 | 2-butene (5%) | 340 | 84.5 | 90.7 | 76.7 |
| | | | Total | | 86.7 | 92.0 | 79.8 |
| Ex. 3 | First reactor | BDP-125 | 1-butene (15%) | 320 | 86.9 | 94.5 | 82.0 |
| | Second reactor | BDP-142 | 2-butene (7.5%) | 340 | 84.2 | 90.5 | 76.3 |
| | | | Total | | 85.1 | 91.9 | 78.2 |
| Ex. 4 | First reactor | BDP-125 | 1-butene (1%) | 320 | 99.6 | 94.2 | 93.8 |
| | Second reactor | BDP-143 | 2-butene (0.5%) | 320 | 79.1 | 92.2 | 72.9 |
| | | | Total | | 85.9 | 92.2 | 79.9 |
| Ex. 5 | First reactor | BDP-125 | 1-butene (1%) | 320 | 99.6 | 94.2 | 93.8 |
| | Second reactor | BDP-146 | 2-butene (0.5%) | 320 | 87.7 | 91.4 | 73.6 |
| | | | Total | | 91.9 | 92.2 | 80.3 |
| Comp. Ex. 1 | First reactor | BDP-125 | 1-butene + 2-butene | 320 | 43.1 | 95.7 | 41.2 |
| Comp. Ex. 2 | Second reactor | BDP-142 | | 320 | 77.5 | 89.3 | 69.2 |
| Comp. Ex. 3 | Second reactor | BDP-143 | | 320 | 84.1 | 91.5 | 76.9 |
| Comp. Ex. 4 | Second reactor | BDP-146 | | 320 | 84.9 | 90.9 | 77.2 |

As can be seen from Table 1 above, Examples 1 to 5, in which catalysts are separately fed to reactors connected in parallel exhibited improved butadiene yield, as compared to Comparative Examples 1 to 4 in which a C4 mixture is treated using a catalyst charged into a single reactor.

The invention claimed is:

1. A method for preparing 1,3-butadiene as a high yield comprising the steps of:
   a) charging a bismuth molybdate-based multimetal elements oxide catalyst wherein the multimetal elements consist of Mo, Bi, Fe, Co, and Cs as a first catalyst in a first reactor as a first catalyst fixed bed;
   b) charging a potassium bismuth molybdate-based multimetal elements oxide catalyst wherein the multimetal elements consist of Mo, Bi, Fe, Co, Cs, and K as a second catalyst into a second reactor connected to the first reactor in parallel as a second catalyst fixed bed; simultaneously or sequentially with step (a),
   c) introducing a C4 mixture comprising 1-butene, 2-butene and normal butane to a distillation column without any solvent to obtain a low-boiling point fraction comprising mainly 1-butene and a high-boiling point fraction comprising mainly 2-butene;
   d) continuously passing the low-boiling point fraction, air and steam to the first reactor to conduct oxidative dehydrogenation;
   e) continuously passing the high-boiling point fraction, air and steam to the second reactor to conduct oxidative dehydrogenation; and
   f) separating reaction effluents obtained from the first reactor and the second reactor into a 1,3-butadiene stream, a normal-butene stream and a C4 mixture stream, wherein the process for preparing the first catalyst comprises: a1) preparing a first solution containing a cesium precursor, a cobalt precursor and an iron precursor, b1) preparing a second solution containing a bismuth precursor, c1) preparing a third solution containing a molybdenum precursor, d1) adding dropwise the second solution to the first solution, followed by mixing, to prepare a fourth solution, e1) adding dropwise the fourth solution to the third solution to prepare a first co-precipitation solution, f1) stirring the first co-precipitation solution for one to two hours and removing moisture to obtain a first solid component, and g1) drying the first solid component in the range of 150 to 200° C. and thermally treating the first solid component in the range of 400 to 600° C. to obtain the bismuth molybdate-based multimetal elements oxide catalyst wherein the multimetal elements consist of Mo, Bi, Fe, Co, and Cs, and wherein the process for preparing the second catalyst comprises: a2) preparing a first solution containing a potassium precursor, a cesium, precursor, a cobalt precursor, an iron precursor and a bismuth precursor, b2) preparing a second solution containing a molybdenum precursor, c2) adding dropwise the second solution to the first solution to prepare a second co-precipitation solution, d2) stirring the second co-precipitation solution for one to two hours and removing moisture to obtain a second solid component, and e2) drying the second solid component in the range of 150 to 200° C. and thermally treating the second solid component in the range of 400 to 600° C. to obtain the potassium bismuth molybdate-based multimetal elements oxide catalyst wherein the multimetal consist of Mo, Bi, Fe, Co, Cs, and K.

2. The method according to claim 1, wherein the first reactor and the second reactor is shell and tube reactor.

3. The method according to claim 1, wherein the C4 mixture comprises 0.5 to 50% by weight of normal-butane, 40 to 99% by weight of normal-butene and 0.5 to 10% by weight of a remaining C4 compound.

4. The method according to claim 3, wherein the C4 mixture comprises 1 -butene, trans-2-butene, cis-2-butene, and normal-butane.

5. The method according to claim 1, wherein the oxidative dehydrogenations in steps d) and e) are conducted at a reaction temperature in the range of 300 to 600° C. and at a gas hourly space velocity (GHSV) in the range of 50 to 5,000 h-1.

6. The method according to claim 1, wherein the distillation column is a two-stage distillation tower having a column plate number of 100 to 200.

7. The method according to claim 1, wherein a weight ratio of 1-butene to 2-butene in the low-boiling point fraction is in the range of 10:0 to 8:2, a weight ratio of 1-butene to 2-butene in the high-boiling point fraction is in the range of 0:10 to 1:9, and a weight ratio of the butene, oxygen, nitrogen, and steam supplied in each reactor is in the range of 1:0.5-2:1 -50:1-50.

8. The method according to claim 1, wherein a conversion of 1-butene into 1,3-butadiene obtained in the first reactor is higher than a conversion of 2-butene into 1,3-butadiene obtained in the second reactor.

9. The method according to claim 1, wherein a selectivity of 1,3-butadiene obtained in the first reactor is higher than a selectivity of 1,3-butadiene obtained in the second reactor.

* * * * *